US007761167B2

(12) United States Patent
Bennett et al.

(10) Patent No.: US 7,761,167 B2
(45) Date of Patent: Jul. 20, 2010

(54) SYSTEMS AND METHODS FOR CLINICIAN CONTROL OF STIMULATION SYSTEMS

(75) Inventors: Maria E. Bennett, Beachwood, OH (US); Kenneth P. Rundle, Independence, OH (US); Stuart F. Rubin, Orange Village, OH (US); James Coburn, Cleveland Heights, OH (US); Danny R. Pack, Avon Lake, OH (US); Robert B. Strother, Willoughby Hills, OH (US); Geoffrey B. Thrope, Shaker Heights, OH (US); Joseph J. Mrva, Euclid, OH (US)

(73) Assignee: Medtronic Urinary Solutions, Inc., Minneapolis, MN (US)

( * ) Notice: Subject to any disclaimer, the term of this patent is extended or adjusted under 35 U.S.C. 154(b) by 238 days.

(21) Appl. No.: 11/541,890

(22) Filed: Oct. 2, 2006

(65) Prior Publication Data
US 2007/0088406 A1    Apr. 19, 2007

Related U.S. Application Data

(63) Continuation-in-part of application No. 11/150,418, filed on Jun. 10, 2005, now Pat. No. 7,239,918, and a continuation-in-part of application No. 11/149,654, filed on Jun. 10, 2005, now Pat. No. 7,565,198, and a continuation-in-part of application No. 11/150,535, filed on Jun. 10, 2005, and a continuation-in-part of application No. 11/517,056, filed on Sep. 7, 2006.

(60) Provisional application No. 60/599,193, filed on Aug. 5, 2004, provisional application No. 60/578,742, filed on Jun. 10, 2004, provisional application No. 60/680, 598, filed on May 13, 2005, provisional application No. 60/801,003, filed on May 17, 2006.

(51) Int. Cl.
*A61N 1/00* (2006.01)
(52) U.S. Cl. ............................. 607/60; 607/30; 607/59
(58) Field of Classification Search .................. 607/30, 607/59, 60
See application file for complete search history.

(56) References Cited

U.S. PATENT DOCUMENTS 3,421,511 A    1/1969    Schwartz et al.

(Continued)

FOREIGN PATENT DOCUMENTS

CA    2121219    10/1995

(Continued)

OTHER PUBLICATIONS

U.S. Appl. No. 60/486,573 file Jul. 11, 2003, Loeb et al.

(Continued)

*Primary Examiner*—Carl H Layno
*Assistant Examiner*—Yun Haeng Lee
(74) *Attorney, Agent, or Firm*—Shumaker & Sieffert, P.A.

(57) ABSTRACT

Systems and methods for programming and logging medical device and patient data are provided. The systems include a handheld device, which is capable of communicating with a medical device, and a base station, which provides connectivity for the handheld device to accomplish various functions such as recharging, programming, data back-up and data entry. The methods comprise the steps of detecting a medical device, obtaining and recording information from the medical device. Additionally, medical device parameters may be modified and the recorded information may be archived for future reference.

13 Claims, 6 Drawing Sheets

U.S. PATENT DOCUMENTS

| | | |
|---|---|---|
| 3,654,933 A | 4/1972 | Hagfors |
| 3,727,616 A | 4/1973 | Lenzkes |
| 3,774,618 A | 11/1973 | Avery |
| 3,870,051 A | 3/1975 | Brindley |
| 3,902,501 A | 9/1975 | Citron et al. |
| 3,926,198 A | 12/1975 | Kolenik |
| 3,939,841 A | 2/1976 | Dohring et al. |
| 3,939,843 A | 2/1976 | Smyth |
| 3,941,136 A | 3/1976 | Bucalo |
| 3,943,932 A | 3/1976 | Woo |
| 3,943,938 A | 3/1976 | Wexler |
| 4,232,679 A | 11/1980 | Schulman |
| 4,254,775 A | 3/1981 | Langer |
| 4,257,423 A | 3/1981 | McDonald |
| 4,262,678 A | 4/1981 | Stokes |
| 4,398,545 A | 8/1983 | Wilson |
| 4,406,288 A | 9/1983 | Horwinski et al. |
| 4,407,303 A | 10/1983 | Akerstrom |
| 4,512,351 A | 4/1985 | Pohndorf |
| 4,519,404 A | 5/1985 | Fleischhacker |
| 4,569,351 A | 2/1986 | Tang |
| 4,573,481 A | 3/1986 | Bullara |
| 4,585,005 A | 4/1986 | Lue et al. |
| 4,585,013 A | 4/1986 | Harris |
| 4,590,689 A | 5/1986 | Rosenberg |
| 4,590,946 A | 5/1986 | Loeb |
| 4,592,360 A | 6/1986 | Lesnick |
| 4,602,624 A | 7/1986 | Naples et al. |
| 4,607,639 A | 8/1986 | Tanagho et al. |
| 4,628,942 A | 12/1986 | Sweeney et al. |
| 4,649,936 A | 3/1987 | Ungar et al. |
| 4,658,515 A | 4/1987 | Oatman |
| 4,703,755 A | 11/1987 | Tanagho et al. |
| 4,716,888 A | 1/1988 | Wesner |
| 4,721,118 A | 1/1988 | Harris |
| 4,739,764 A | 4/1988 | Lue et al. |
| 4,750,499 A | 6/1988 | Hoffer |
| 4,771,779 A | 9/1988 | Tanagho et al. |
| 4,793,353 A | 12/1988 | Borkan |
| 4,835,372 A | 5/1989 | Gombrich |
| 4,920,979 A | 5/1990 | Bullara |
| 4,926,875 A | 5/1990 | Rabinovitz et al. |
| 4,934,368 A | 6/1990 | Lynch |
| 4,940,065 A | 7/1990 | Tanagho et al. |
| 4,989,617 A | 2/1991 | Memberg et al. |
| 5,095,905 A | 3/1992 | Klepinski |
| 5,113,869 A | 5/1992 | Nappholz et al. |
| 5,154,172 A | 10/1992 | Terry, Jr. et al. |
| 5,215,086 A | 6/1993 | Terry, Jr. et al. |
| 5,222,494 A | 6/1993 | Baker, Jr. |
| D337,820 S | 7/1993 | Hooper et al. |
| 5,235,980 A | 8/1993 | Varrichio et al. |
| 5,257,634 A | 11/1993 | Kroll |
| 5,265,608 A | 11/1993 | Lee et al. |
| 5,282,845 A | 2/1994 | Bush et al. |
| 5,289,821 A | 3/1994 | Swartz |
| 5,300,107 A | 4/1994 | Stokes et al. |
| 5,324,322 A | 6/1994 | Grill et al. |
| 5,330,515 A | 7/1994 | Rutecki et al. |
| 5,335,664 A | 8/1994 | Nagashima |
| 5,344,439 A | 9/1994 | Otten |
| 5,369,257 A | 11/1994 | Gibbon |
| 5,370,671 A | 12/1994 | Maurer et al. |
| 5,397,338 A | 3/1995 | Grey et al. |
| 5,400,784 A | 3/1995 | Durand et al. |
| 5,411,537 A | 5/1995 | Munshi et al. |
| 5,449,378 A | 9/1995 | Schouenborg |
| 5,454,840 A | 10/1995 | Krakovsky et al. |
| 5,461,256 A | 10/1995 | Yamada |
| 5,476,500 A | 12/1995 | Fain et al. |
| 5,480,416 A | 1/1996 | Garcia et al. |
| 5,486,202 A | 1/1996 | Bradshaw |
| 5,487,756 A | 1/1996 | Kallesoe et al. |
| 5,505,201 A | 4/1996 | Grill et al. |
| 5,531,778 A | 7/1996 | Maschino et al. |
| 5,540,730 A | 7/1996 | Terry, Jr. et al. |
| 5,562,717 A | 10/1996 | Tippey et al. |
| 5,588,960 A | 12/1996 | Edwards et al. |
| 5,607,461 A | 3/1997 | Lathrop |
| 5,634,462 A | 6/1997 | Tyler et al. |
| 5,645,586 A | 7/1997 | Meltzer |
| 5,669,161 A | 9/1997 | Huang |
| 5,683,432 A | 11/1997 | Goedeke et al. |
| 5,683,447 A | 11/1997 | Bush et al. |
| 5,690,693 A | 11/1997 | Wang et al. |
| 5,702,431 A | 12/1997 | Wang et al. |
| 5,713,939 A | 2/1998 | Nedungadi et al. |
| 5,716,384 A * | 2/1998 | Snell .......................... 607/30 |
| 5,722,482 A | 3/1998 | Buckley |
| 5,722,999 A | 3/1998 | Snell |
| 5,733,322 A | 3/1998 | Starkebaum |
| 5,741,313 A | 4/1998 | Davis et al. |
| 5,741,319 A | 4/1998 | Woloszko et al. |
| 5,752,977 A | 5/1998 | Grevious |
| 5,755,767 A | 5/1998 | Doan et al. |
| 5,759,199 A | 6/1998 | Snell |
| 5,807,397 A | 9/1998 | Barreras |
| 5,824,027 A | 10/1998 | Hoffer et al. |
| 5,843,141 A | 12/1998 | Bischoff et al. |
| 5,857,968 A | 1/1999 | Benja-Athon |
| 5,861,015 A | 1/1999 | Benja-Athon |
| 5,861,016 A | 1/1999 | Swing |
| 5,899,933 A | 5/1999 | Bhadra et al. |
| 5,919,220 A | 7/1999 | Stieglitz et al. |
| 5,922,015 A | 7/1999 | Schaldach |
| 5,938,596 A | 8/1999 | Woloszko et al. |
| 5,948,006 A | 9/1999 | Mann |
| 5,957,951 A | 9/1999 | Cazaux et al. |
| 5,984,854 A | 11/1999 | Ishikawa et al. |
| 6,004,662 A | 12/1999 | Buckley |
| 6,016,451 A | 1/2000 | Sanchez-Rodarte |
| 6,026,328 A | 2/2000 | Peckham et al. |
| 6,055,456 A | 4/2000 | Gerber |
| 6,055,457 A | 4/2000 | Bonner |
| 6,061,596 A | 5/2000 | Richmond et al. |
| 6,091,995 A | 7/2000 | Ingle et al. |
| 6,125,645 A | 10/2000 | Horn |
| 6,126,611 A | 10/2000 | Bourgeois et al. |
| 6,166,518 A | 12/2000 | Echarri et al. |
| 6,169,925 B1 | 1/2001 | Villaseca et al. |
| 6,181,965 B1 | 1/2001 | Loeb et al. |
| 6,181,973 B1 | 1/2001 | Ceron et al. |
| 6,185,452 B1 | 2/2001 | Schulman et al. |
| 6,200,265 B1 | 3/2001 | Walsh et al. |
| 6,208,894 B1 | 3/2001 | Schulman et al. |
| 6,212,431 B1 | 4/2001 | Hahn et al. |
| 6,216,038 B1 | 4/2001 | Hartlaub et al. |
| 6,240,316 B1 | 5/2001 | Richmond et al. |
| 6,240,317 B1 | 5/2001 | Villaseca et al. |
| 6,249,703 B1 | 6/2001 | Stanton |
| 6,257,906 B1 | 7/2001 | Price et al. |
| 6,266,557 B1 | 7/2001 | Roe et al. |
| 6,275,737 B1 | 8/2001 | Mann |
| 6,292,703 B1 | 9/2001 | Meier et al. |
| 6,308,101 B1 | 10/2001 | Faltys et al. |
| 6,308,105 B1 | 10/2001 | Duysens et al. |
| 6,319,208 B1 | 11/2001 | Abita et al. |
| 6,319,599 B1 | 11/2001 | Buckley |
| 6,321,124 B1 | 11/2001 | Cigaina |
| 6,338,347 B1 | 1/2002 | Chung |
| 6,345,202 B2 | 2/2002 | Richmond et al. |
| 6,360,750 B1 | 3/2002 | Gerber et al. |
| 6,381,496 B1 | 4/2002 | Meadows et al. |
| 6,409,675 B1 | 6/2002 | Turcott |

| | | |
|---|---|---|
| 6,432,037 B1 | 8/2002 | Eini et al. |
| 6,442,432 B2 | 8/2002 | Lee |
| 6,442,433 B1 | 8/2002 | Linberg |
| 6,445,955 B1 | 9/2002 | Michelson et al. |
| 6,449,512 B1 | 9/2002 | Boveja et al. |
| 6,450,172 B1 | 9/2002 | Hartlaub et al. |
| 6,453,198 B1 | 9/2002 | Torgerson et al. |
| 6,456,866 B1 | 9/2002 | Tyler et al. |
| 6,464,672 B1 | 10/2002 | Buckley |
| 6,482,154 B1 | 11/2002 | Haubrich et al. |
| 6,493,587 B1 | 12/2002 | Eckmiller et al. |
| 6,493,881 B1 | 12/2002 | Picotte |
| 6,505,074 B2 | 1/2003 | Boveja et al. |
| 6,505,077 B1 | 1/2003 | Kast et al. |
| 6,510,347 B2 | 1/2003 | Borkan |
| 6,516,227 B1 | 2/2003 | Meadows et al. |
| 6,535,766 B1 | 3/2003 | Thompson et al. |
| 6,542,776 B1 | 4/2003 | Gordon et al. |
| 6,553,263 B1 | 4/2003 | Meadows et al. |
| 6,574,510 B2 | 6/2003 | Von Arx et al. |
| 6,591,137 B1 | 7/2003 | Fischell et al. |
| 6,597,954 B1 | 7/2003 | Pless et al. |
| 6,600,956 B2 | 7/2003 | Maschino et al. |
| 6,607,500 B2 | 8/2003 | Da Silva et al. |
| 6,613,953 B1 | 9/2003 | Altura |
| 6,622,037 B2 | 9/2003 | Kasano |
| 6,622,048 B1 | 9/2003 | Mann et al. |
| 6,641,533 B2 | 11/2003 | Causey et al. |
| 6,643,552 B2 | 11/2003 | Edell et al. |
| 6,650,943 B1 | 11/2003 | Whitehurst et al. |
| 6,652,449 B1 | 11/2003 | Gross et al. |
| 6,658,300 B2 | 12/2003 | Gorari et al. |
| 6,660,265 B1 | 12/2003 | Chen et al. |
| 6,672,895 B2 | 1/2004 | Scheiner |
| 6,684,109 B1 | 1/2004 | Osypka |
| 6,687,543 B1 | 2/2004 | Isaac |
| 6,701,188 B2 | 3/2004 | Stroebel et al. |
| 6,721,602 B2 | 4/2004 | Engmark et al. |
| 6,735,474 B1 | 5/2004 | Loeb et al. |
| 6,735,475 B1 | 5/2004 | Whitehurst et al. |
| 6,754,538 B2 | 6/2004 | Linberg |
| 6,775,715 B2 | 8/2004 | Spitaels et al. |
| 6,804,558 B2 | 10/2004 | Haller et al. |
| 6,836,684 B1 | 12/2004 | Rijkhoff et al. |
| 6,836,685 B1 | 12/2004 | Fitz |
| 6,845,271 B2 | 1/2005 | Fang et al. |
| 6,855,410 B2 | 2/2005 | Buckley |
| 6,856,506 B2 | 2/2005 | Doherty |
| 6,859,364 B2 | 2/2005 | Yuasa et al. |
| 6,862,480 B2 | 3/2005 | Cohen et al. |
| 6,868,288 B2 | 3/2005 | Thompson |
| 6,891,353 B2 | 5/2005 | Tsukamoto |
| 6,895,280 B2 | 5/2005 | Meadows et al. |
| 6,904,324 B2 | 6/2005 | Bishay |
| 6,907,293 B2 | 6/2005 | Grill et al. |
| 6,907,295 B2 | 6/2005 | Gross et al. |
| 6,920,359 B2 | 7/2005 | Meadows et al. |
| 6,925,330 B2 | 8/2005 | Kleine |
| 6,928,320 B2 | 8/2005 | King |
| 6,937,894 B1 | 8/2005 | Isaac et al. |
| 6,941,171 B2 | 9/2005 | Mann et al. |
| 6,963,780 B2 | 11/2005 | Ruben et al. |
| 6,974,411 B2 | 12/2005 | Belson |
| 6,985,773 B2 | 1/2006 | Von Arx |
| 6,990,376 B2 | 1/2006 | Tanagho |
| 6,993,393 B2 | 1/2006 | Von Arx et al. |
| 6,999,819 B2 | 2/2006 | Swoyer et al. |
| 7,031,768 B2 | 4/2006 | Anderson et al. |
| 7,047,078 B2 | 5/2006 | Boggs et al. |
| 7,078,359 B2 | 7/2006 | Stepanian et al. |
| 7,101,607 B2 | 9/2006 | Mollendorf |
| 7,103,923 B2 | 9/2006 | Picotte |
| 7,118,801 B2 | 10/2006 | Ristic-Lehmann |
| 7,136,695 B2 | 11/2006 | Pless |
| 7,167,756 B1 | 1/2007 | Torgerson et al. |
| 7,177,690 B2 | 2/2007 | Woods et al. |
| 7,177,698 B2 | 2/2007 | Klosterman |
| 7,187,968 B2 | 3/2007 | Wolf |
| 7,187,983 B2 | 3/2007 | Dahlberg et al. |
| 7,191,012 B2 | 3/2007 | Boveja et al. |
| 7,198,603 B2 | 4/2007 | Penner et al. |
| 7,225,032 B2 | 5/2007 | Schmeling et al. |
| 7,239,918 B2 | 7/2007 | Strother et al. |
| 7,254,448 B2 | 8/2007 | Almendinger et al. |
| 7,269,457 B2 | 9/2007 | Shafer et al. |
| 7,280,872 B1 | 10/2007 | Mosesov et al. |
| 7,283,867 B2 | 10/2007 | Strother |
| 7,317,947 B2 | 1/2008 | Wahlstrand |
| 7,328,068 B2 | 2/2008 | Spinelli et al. |
| 7,342,793 B2 | 3/2008 | Ristic-Lehmann |
| 7,343,202 B2 | 3/2008 | Mrva et al. |
| 7,369,897 B2 | 5/2008 | Boveja |
| 7,376,467 B2 | 5/2008 | Thrope |
| 7,437,193 B2 | 10/2008 | Parramon et al. |
| 7,443,057 B2 | 10/2008 | Nunally |
| 7,475,245 B1 | 1/2009 | Healy et al. |
| 7,499,758 B2 | 3/2009 | Cates et al. |
| 7,565,198 B2 | 7/2009 | Bennett |
| 2001/0022719 A1* | 9/2001 | Armitage et al. ............ 361/681 |
| 2002/0019652 A1 | 2/2002 | Da Silva et al. |
| 2002/0055779 A1 | 5/2002 | Andrews |
| 2002/0077572 A1 | 6/2002 | Fang et al. |
| 2002/0164474 A1 | 11/2002 | Buckley |
| 2003/0018365 A1 | 1/2003 | Loeb |
| 2003/0065368 A1 | 4/2003 | Van Der Hoeven |
| 2003/0074030 A1 | 4/2003 | Leyde et al. |
| 2003/0078633 A1 | 4/2003 | Firlik et al. |
| 2003/0114897 A1 | 6/2003 | Von Arx et al. |
| 2003/0114905 A1 | 6/2003 | Kuzma |
| 2003/0120259 A1 | 6/2003 | Mickley |
| 2003/0220673 A1 | 11/2003 | Snell |
| 2003/0235029 A1* | 12/2003 | Doherty et al. ............ 361/683 |
| 2004/0030360 A1 | 2/2004 | Eini et al. |
| 2004/0088024 A1 | 5/2004 | Firlik et al. |
| 2004/0093093 A1 | 5/2004 | Andrews |
| 2004/0098068 A1 | 5/2004 | Carbunaru et al. |
| 2004/0147886 A1 | 7/2004 | Bonni |
| 2004/0150963 A1 | 8/2004 | Holmberg et al. |
| 2004/0209061 A1 | 10/2004 | Farnworth |
| 2005/0038491 A1 | 2/2005 | Haack |
| 2005/0055063 A1 | 3/2005 | Loeb et al. |
| 2005/0080463 A1 | 4/2005 | Stahmann |
| 2005/0143787 A1 | 6/2005 | Boveja et al. |
| 2005/0149146 A1 | 7/2005 | Boveja et al. |
| 2005/0175799 A1 | 8/2005 | Farnworth |
| 2005/0192526 A1 | 9/2005 | Biggs et al. |
| 2005/0278000 A1 | 12/2005 | Strother |
| 2006/0004421 A1 | 1/2006 | Bennett et al. |
| 2006/0025829 A1 | 2/2006 | Armstrong et al. |
| 2006/0033720 A1 | 2/2006 | Robbins |
| 2006/0035054 A1 | 2/2006 | Stepanian et al. |
| 2006/0100673 A1 | 5/2006 | Koinzer et al. |
| 2006/0122660 A1 | 6/2006 | Boveja et al. |
| 2006/0173507 A1 | 8/2006 | Mrva |
| 2006/0184208 A1 | 8/2006 | Boggs et al. |
| 2006/0271112 A1 | 11/2006 | Martinson et al. |
| 2007/0060967 A1 | 3/2007 | Strother |
| 2007/0100411 A1 | 5/2007 | Bonde |
| 2007/0123952 A1 | 5/2007 | Strother |
| 2007/0239224 A1 | 10/2007 | Bennett et al. |
| 2008/0071322 A1 | 3/2008 | Mrva et al. |
| 2008/0097564 A1 | 4/2008 | Lathrop |

| | | |
|---|---|---|
| 2008/0132969 A1 | 6/2008 | Bennett et al. |

FOREIGN PATENT DOCUMENTS

| | | |
|---|---|---|
| WO | WO2000/019939 | 4/2000 |
| WO | WO2001/083029 | 11/2001 |
| WO | WO02003/092227 | 4/2003 |
| WO | WO2006/055547 | 5/2006 |
| WO | WO2009/058984 | 5/2009 |

OTHER PUBLICATIONS

2004 Advanced Bionics Corporation Patient System Handbook.
2004 Advanced Bionics Corporation Physician Implant Manual.
2004 Advanced Bionics Corporation Summary of Safety and Effectiveness, pp. 1-18.
2005 Advanced Neuromodulation Systems, Inc.; ANS Medical — Determining Chronic Pain Causes and Treatments; website: www.ans-medical.com/medicalprofessional/phvsician/rechargeableipgsystems.cfm.
2005 Cyberonics Vns Therapy Website: www.vnstherapy.com/epilepsy/hcp/forsurgeons/implantedcomponents.aspx.
A Breakthrough in Advanced Materials, Aspen Aerogels, Inc. (1 pg) www.aerogels.com, 2003.
Aug. 2002 Physician's Manual; Cyberonics Models 100 and 101 NeuroCybernetic Prosthesis System, NCP Pulse Generator, pp. 1-92.
Bemelmans, Bart L.H., et al., "Neuromodulation by Implant for Treating Lower Urinary Tract Symptoms and Dysfunction," Eur. Urol. 1999 Aug. 36(2): 81-91.
Bower, W.F., et al., "A Urodynamic Study of Surface Neuromodulation versus Sham in Detrusor Instability and Sensory Urgency", J. Urology 1998; 160: 2133-2136.
Brindley, G., et al., "Sacral Anterior Root Stimulators for Bladder Control in Paraplegia", Paraplegia 1982; 20(6):365-381.
Corbett, Scott S., http://crisp.cit.nih.gov/ Abstract, High-Density Liquid Crystal Polymer Cochlear Electrodes, downloaded Sep. 18, 2006.
Caldwell, C. (1971) Multielectrode Electrical Stimulation of Nerve, in Development of Orthotic Systems using Functional Electrical Stimulation and Myoelectric Control, Final Report Project #19-P-58391-F-01, University of Lublinana, Faculty of Electrical Engineering, Lubjiana, Yugoslavia.
Craggs, M., and McFarlane, J.P., "Neuromodulation of the Lower Urinary Tract," Experimental Physiology, 84, 149-160 1999.
Crampon et al., "Nerve Cuff Electrode with Shape Memory Alloy Armature: Design and Fabrication", *Bio-Medical Materials and Engineering* 12 (2002) 397-410.
Craggs, M., et al., "Aberrant reflexes and function of the pelvic organs following spinal cord injury in man", Autonomic Neuroscience: Basic & Clinical, 126-127 (2006), 355370.
Crampon et al., "New Easy to Install Nerve Cuff Electrode Using Shape Memory Alloy Armature", *Artificial Organs*, 23(5):392-395, 1999.
Dalmose, a.L., et al., "Conditional Stimulation of the Dorsal Penile/Clitoral Nerve", Neurourol Urodyn 2003; 22(2):130-137.
Edell, David J., PhD, Boston Healthcare Research Device, Feb. 15, 2006.
Fossberg, E., et al. "Maximal Electrical Stimulation in the Treatment of Unstable Detrusor and Urge Incontinence", Eur Urol 1990; 18:120-123.
Grill, et al,, "Emerging clinical applications of electrical stimulation: opportunities for restoration of function", Journal of Rehabilitation Research and Development, vol. 38, No. 6, Nov./Dec. 2001.
Grill, W. M., Mortimer, J.T., (1996) Quantification of recruitment properties of multiple contact cuff electrodes, IEEE Transactions on Rehabilitation Engineering 4(2):49-62.
Grill, W.M., (2001) "Selective Activation of the Nervous System for Motor System Neural Prosthesis" in Intelligent Systems and Technologies in Rehabilitation Engineering, H-N. L. Teodorescu, L. C. Jain, Eds., CRC Press, pp. 211-241.
Gustafson, K., et al. "A Urethral Afferent Mediated Excitatory Bladder Reflex Exists in Humans", Neurosci Lett 2004: 360(1-2):9-12.
Gustafson, K., et al., "A Catheter Based Method to Activate Urethral Sensory Nerve Fibers", J Urol 2003: 170(1):126-129.

Jezernik, S., "Electrical Stimulation for the Treatment of Bladder Dysfunction: Current Status and Future Possibilities", Neurol. Res. 2002: 24:413-30.
Jezernik, S., et al., "Detection and inhibition of hyper-reflexia-like bladder contractions in the cat by sacral nerve root recording and electrical stimulation," Neurourology and Urodynamics, 20(2), 215-230 (2001).
Jiang, C., et al., "Prolonged Increase in Micturition Threshold Volume by Anogenital Afferent Stimulation in the Rat", Br J. Urol. 1998: 82(3):398-403.
Jiang, C-H., et al., "Prolonged enhancement of the micturition reflex in the cat by repetitive stimulation of bladder afferents," Journal of Physiology, 517.2 599-605 (1999).
Juenemann, K., et al., "Clinical Significance of Sacral and Pudendal Nerve Anatomy:, J. Urol. 1988; 139(1):74-80.
Lee, Y.H., et al., "Self-Controlled dorsal penile nerve stimulation to inhibit bladder hyperreflexia in incomplete spinal injury: A case report," Arch Phys Med Rehabil., 83, 273-7 (2002).
Loeb et al., "Cuff Electrodes for Chronic Stimulation and Recording of Peripheral Nerve Activity", *Journal of Neuroscience Methods*, 64 (1996), 95-103.
Madersbacher, H., "Urinary Urge and Reflex Incontinence:, Urologe a. 1991: 30(4): 215222 (Abstract only, article in German).
Mar. 2002 Physician's Manual; Cyberonics Model 201 NeuroCybernetic Prosthesis (NCP) Programming Wand, pp. 1-18.
Mazieres, L., et al., "Bladder Parasympathetic Response to Electrical Stimulation of Urethral Afferents in the Cat", Neurol Urodynam 1997; 16:471-472.
Mazieres, L., et al., "The C Fibre Reflex of the Cat Urinary Bladder", J. Physiol 1998; 513 (Pt 2):531-541.
McNeal, D.R., (1974) Selective Stimulation, in Annual Reports of Progress, Rehabilitation Engineering Center, Ranchio Los Amigos Hospital, Downey, CA, pp. 24-25.
McNeal, D.R., Bowman, B.R., (1985) Selective activation of muscles using peripheral nerve electrodes. Med. And Biol. Eng. And Comp., 23:249-253.
Modern Plastics Worldwide, Notables: 10 Waves of the Future by Modern Plastics Editorial Staff, Sample Molding in Progress: Sep. 01, 2005.
Nakamura, M., et al., "Bladder Inhibition by Penile Electrical Stimulation", Br J Urol 1984: 56:413-415.
Naples, et al., "A Spiral Nerve Cuff Electrode for Peripheral Nerve Stimulation", IEEE *Transactions on Biomedical Engineering*, vol. 35, No. 11, Nov. 1988.
NeuroControl Corp., NeuroControl StiM System brochure.
NeuroControl Corp., the NeuroControl StiM System, "World's First Miniturized Multi-Channel Programmable Neuromuscular Stimulator" brochure.
Nissenkorn, Israel, and De Jong, Peter R., 2005 Biocontrol Medical Article: "Lower Urinary Tract," pp. 1253-1258.
Nov. 21, 2001 Advanced Neuromodulation Systems, Inc. (ANS) Summary of Safety and Effectiveness Data, pp. 1-17.
Oct. 2001 Advanced Neuromodulation Systems, Inc., ANS Genesis Neurostimulation System Programmer User's Guide.
Oliver, S., et al., "Measuring the Sensations of Urge and Bladder Filling During Cystometry in Urge Incontinence and the Effects of Neuromodulation", Neurourol Urodyn 2003: 22:7-16.
Previnaire, J.G., "Short-Term Effect of Pudendal Nerve Electrical Stimulation on Detrusor Hyperreflexia in Spinal Cord Injury Patients: Importance of Current Strength", Paraplegia 1996: 34:95-99.
Rijkhoff, N., et al., "Urinary Bladder Control by Electrical Stimulation: Review of Electrical Stimulation Techniques in Spinal Cord Injury", Neurourol Urodyn 1997; 16(1):39-53.
Riley, George A., PhD, www.flipchips.com Advanced Packaging —Water Level Hermetic Cavity Packaging, originally published in Advanced Packaging Magazine, May 2004.
Riley, George A., PhD, www.flipchips.com, Tutorial 31 —Jun. 2003, a survey of Water Level Hermetic Cavity Chip Scale Packages for RF Applications.
Romero et al., "Neural Morphological Effects of Long-Term Implantation of the Self-Sizing Spiral Cuff Nerve Electrode", *Medical & Biological Engineering & Computing*, 2001, vol. 39, pp. 90-100.

Sahin et al., " Spiral Nerve Cuff Electrode for Recordings of Respiratory Output", *The Spiral Nerve Cuff Electrode*, 1997 American Physiological Society, pp. 317-322.

Schmidt, R.A., "Applications of Neurostimulation in Urology", 1988; 7:585-92.

Starbuck, D.L. (1965) Myo-electric control of paralyzed muscles. IEEE Transactions on Biomedical Engineering 12(3):169-172, Jul.-Oct.

Spinelli, M., et al., "A New Minimally Invasive Procedure for Pudendal Nerve Stimulation to Treat Neurogenic Bladder: Description of the Method and Preliminary Data", Neurourol and Urodyn. 2005: 24:305-309.

Starbuck, D. L., Mortimer, J.T., Sheally, C.N., Reswick, J.B. (1966) an implantable electrodes system for nerve stimulation, Proc 19th Ann. Conf. on Eng. In Med. And Biol. 8:38.

Sundin, T., et al., "Detrusor inhibition induced from mechanical stimulation of the anal region and from electrical stimulation of pudendal nerve afferents," Investigative Urology, 5, 374-8 (1974).

Sweeney, et al., "A Nerve Cuff Technique for Selective Excitation of Peripheral Nerve Trunk Regions", *IEEE Transactions on Biomedical Engineering*, vol. 37, No. 7, pp. 706-715, Jul. 1990.

Talaat, M., "Afferent Impulses in the Nerves Supplying the Urinary Bladder", Journal of Physiology 1937: 89-1-13.

Tanagho, E.A., et al. "Electrical Stimulation in the Clinical Management of the Neurogenic Bladder", J. Urol. 1988; 140:1331-1339.

Tyler, et al., "Chronic Response of the Rat Sciatic Nerve to the Flat Interface Nerve Electrode", *Annals of Biomedical Engineering*, vol. 31, pp. 633-642, 2003.

Veraart, C., Grill, W.M., Mortimer, J.T., (1993) Selective control of muscle activation with a multipolar nerve cuff electrode, IEEE Trans. Biomed. Engineering 40:640-653.

Vodusek, D.B., et al. "Detrusor Inhibition Induced by Stimulation of Pudendal Nerve Afferents", Neuroul and Urodyn., 1986; 5:381-389.

Wheeler, et al., "Bladder inhibition by penile nerve stimulation in spinal cord injury patients", The Journal of Urology, 147(1), 100-3 (1992).

Wheeler, et al., "Management of Incontinent SCI patients with Penile Stimulation; Preliminary Results," J. Am. Paraplegia Soc. Apr. 1994: 17(2):55-9.

www.devicelink.com, MPMN, May 2004, Liquid-Crystal Polymer Meets the Challenges of RF Power Packaging; the plastic air-cavity packages are hermetically sealed using a proprietary process, Susan Wallace.

www.foster-millencom, Project Examples, Packaging for Implantable Electronics, Foster-Miller, Inc. Feb. 15, 2006.

Yang, C., et al., "Peripheral Distribution of the Human Dorsal Nerve of the Penis", J. Urol 1998; 159(6):1912-6, discussion 1916.

www.machinedesign.texterity.com, Vacuum-Formed Films for Fit and Function, High-Performance Films can Replace Injection-Molded Plastics When Space is at a Premium, David Midgley, Welch Fluorocarbon Inc., Dover, NH Oct. 07, 2004.

PCT Search Report and Written Opinion dated Feb. 2, 2009 for PCT/US08/081762.

Reply to Written Opinion dated Nov. 13, 2008 for PCT/US07/014396.

Notification of Transmission of IPRP dated Jun 26, 2009 for PCT/US07/014396.

Notification of Transmittal of the International Search Report and Written Opinion dated Jul. 18,2008 for PCT/US08/002540.

PCT Written Opinion dated Feb 2, 2009 for PCTCUS08/081762 (10 pgs.).

* cited by examiner

SYSTEMS AND METHODS FOR CLINICIAN CONTROL OF STIMULATION SYSTEMS

RELATED APPLICATIONS

This application is a continuation-in-part of U.S. patent application Ser. No. 11/150,418, filed 10 Jun. 2005, now U.S. Pat. No. 7,239,918, and entitled "Implantable Pulse Generator for Providing Functional and/or Therapeutic Stimulation of Muscles and/or Nerves and/or Central Nervous System Tissue," which claims the benefit of U.S. Provisional Patent Application Ser. No. 60/599,193, filed 5 Aug. 2004, and entitled "Implantable Pulse Generator for Providing Functional and/or Therapeutic Stimulation of Muscles and/or Nerves," both of which are incorporated herein by reference.

This application is also a continuation-in-part of U.S. patent application Ser. No. 11/149,654, filed 10 Jun. 2005, now U.S. Pat. No. 7,565,198, and entitled "Systems and Methods for Bilateral Stimulation of Left and Right Branches of the Dorsal Genital Nerves to Treat Dysfunctions, Such as Urinary Incontinence," which claims the benefit of U.S. Provisional Patent Application Ser. No. 60/578,742, filed 10 Jun. 2004, and entitled "Systems and Methods for Bilateral Stimulation of Left and Right Branches of the Dorsal Genital Nerves to Treat Dysfunctions, Such as Urinary Incontinence," both of which are incorporated herein by reference.

This application is also a continuation-in-part of co-pending U.S. patent application Ser. No. 11/150,535, filed 10 Jun. 2005, and entitled "Implantable Pulse Generator for Providing Functional and/or Therapeutic Stimulation of Muscles and/or Nerves and/or Central Nervous System Tissue," which claims the benefit of U.S. Provisional Patent Application Ser. No. 60/680,598, filed 13 May 2005, and entitled "Implantable Pulse Generator for Providing Functional and/or Therapeutic Stimulation of Muscles and/or Nerves and/or Central Nervous System Tissue," both of which are incorporated herein by reference.

This application is also a continuation-in-part of co-pending U.S. patent application Ser. No. 11/517,056, filed 7 Sep. 2006, and entitled "Implantable Pulse Generator Systems And Methods For Providing Functional And/Or Therapeutic Stimulation Of Muscles And/Or Nerves And/Or Central Nervous System Tissue," which claims the benefit of U.S. Provisional Patent Application Ser. No. 60/801,003, filed 17 May 2006, and entitled "Implantable Pulse Generator For Providing Functional And/Or Therapeutic Stimulation Of Muscles And/Or Nerves And/Or Central Nervous System Tissue," both of which are incorporated herein by reference.

BACKGROUND OF THE INVENTION

The invention relates generally to systems and methods for programming, tracking and recording data from electronic devices. More specifically, the present invention relates to systems and methods for programming, tracking and recording data from medical devices, and especially implantable medical devices (IMDs).

Medical devices, specifically IMDs, are commonly used today to treat patients suffering from various ailments, including by way of example, pain, incontinence, movement disorders such as epilepsy, Parkinson's disease, and spasticity. Additional IMD therapies appear promising to treat a variety of other medical conditions, including physiological, psychological, and emotional conditions. As the number of IMD therapies increases, so do the demands placed on these medical devices.

Known IMDs, such as, cardiac pacemakers, tachyarrhythmia control devices, drug delivery devices, and nerve stimulators, provide treatment therapy to various portions of the body. While the present invention may be used with various medical devices, by way of example and illustration, an implantable pulse generator (IPG) device will be discussed to illustrate the advantages of the invention. In the case of providing electrical stimulation to a patient, an IPG is implanted within the body. The IPG is coupled to one or more electrodes to deliver electrical stimulation to select portions of the patient's body. Neuromuscular stimulation (the electrical excitation of nerves and/or muscle to directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes.

There exist both external and implantable devices for providing beneficial results in diverse therapeutic and functional restorations indications. The operation of these devices typically includes the use of an electrode placed either on the external surface of the skin, a vaginal or anal electrode, or a surgically implanted electrode. Implantable medical devices may be programmable and/or rechargeable, and the devices may log data, which are representative of the operating characteristics over a length of time. While existing systems and methods provide the capability of programming or recharging IMDs, many limitations and issues still remain.

Implantable devices have provided an improvement in the portability of neurological stimulation devices, but there remains the need for continued improvement in the programming and data management related to such devices. Medical devices are often controlled using microprocessors with resident operating system software. This operating system software may be further broken down into subgroups including system software and application software. The system software controls the operation of the medical device while the application software interacts with the system software to instruct the system software on what actions to take to control the medical device based upon the actual application of the medical device.

As the diverse therapeutic and functional uses of IMDs increase, and become more complex, system software having a versatile interface is needed to play an increasingly important role. This interface allows the system software to remain generally consistent based upon the particular medical device, and allows the application software to vary greatly depending upon the particular application. As long as the application software is written so it can interact with the interface, and in turn the system software, the particular medical device can be used in a wide variety of applications with only changes to application specific software. This allows a platform device to be manufactured in large, more cost effective quantities, with application specific customization occurring at a later time.

While handheld programmers are generally known in the art, there exist many gaps in the methods for programming and tracking specific system or patient data related to medical devices, especially those of the implanted type. Specifically, the art is lacking cohesive systems and methods for programming medical devices, logging medical device and patient data, recharging portable control devices and providing hard copies of information, such as patient or system information.

SUMMARY OF THE INVENTION

Filling the identified needs, the present invention provides systems and methods for programming medical devices, logging medical device and patient data, recharging portable control devices and providing hard copies of information, such as patient or system information.

Generally, the systems comprise a handheld device and a base station. The handheld device provides mobile data management and medical device communications capabilities. The base station provides a connectivity point for the handheld unit, thereby allowing recharge of the handheld unit, printing from the handheld unit, the base station, or the handheld unit while residing in the base station, or data entry or modification, among other functions.

Generally, the methods comprise the steps of detecting a medical device and obtaining and recording information from the medical device. Further, medical device parameters may be altered and information archived for future reference.

The systems and methods of the present invention fill the void in the prior art by providing a convenient means to program medical devices, to log data recorded by, and parameters of, medical devices and the ability to create a hard copy of information, such as recorded device or patient data or system parameters.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

System

Figure 1:
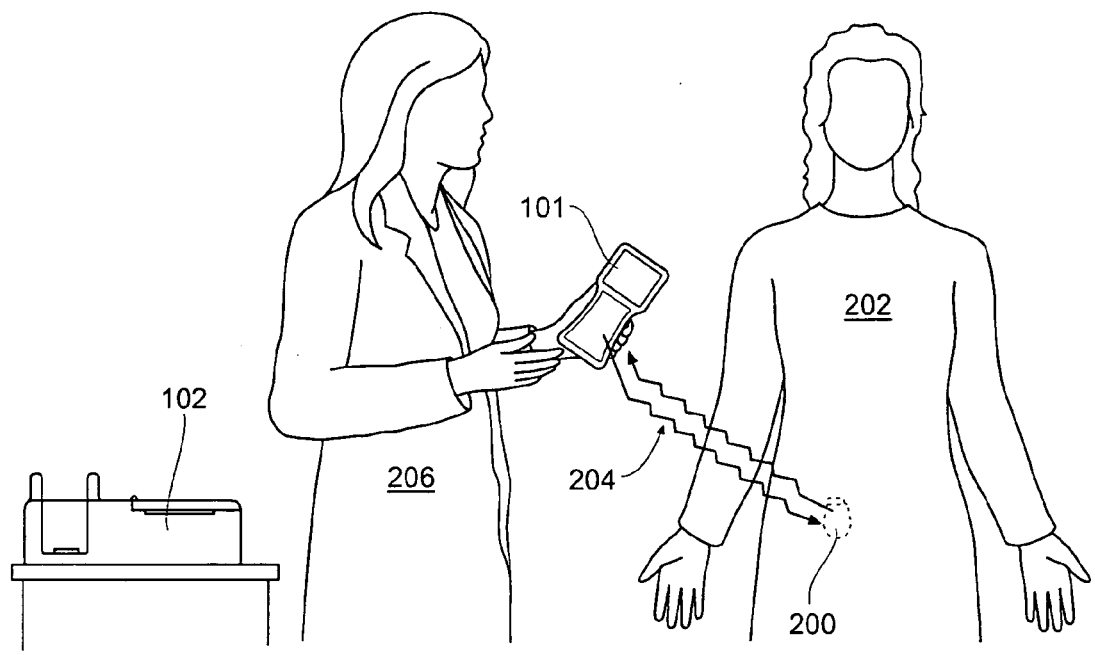
FIG. 1 is an elevation view of a system according to the present invention in use.

FIG. 1 depicts an embodiment of a system 100 according to the present invention in use. The clinical programmer system 100 comprises generally two subsystems: a mobile, handheld device 101 and a base station 102. The handheld device 101 communicates with a medical device 200, which may be implanted in a patient 202, over a first communication channel 204 and provides an interface to a user, which may be a clinician 206, to enable control of the handheld device 101 and the medical device 200. As stated above, while the present invention may be used with various medical devices 200, by way of example and illustration, an implantable pulse generator (IPG) device will be discussed to illustrate the advantages of the invention.

Figure 2:
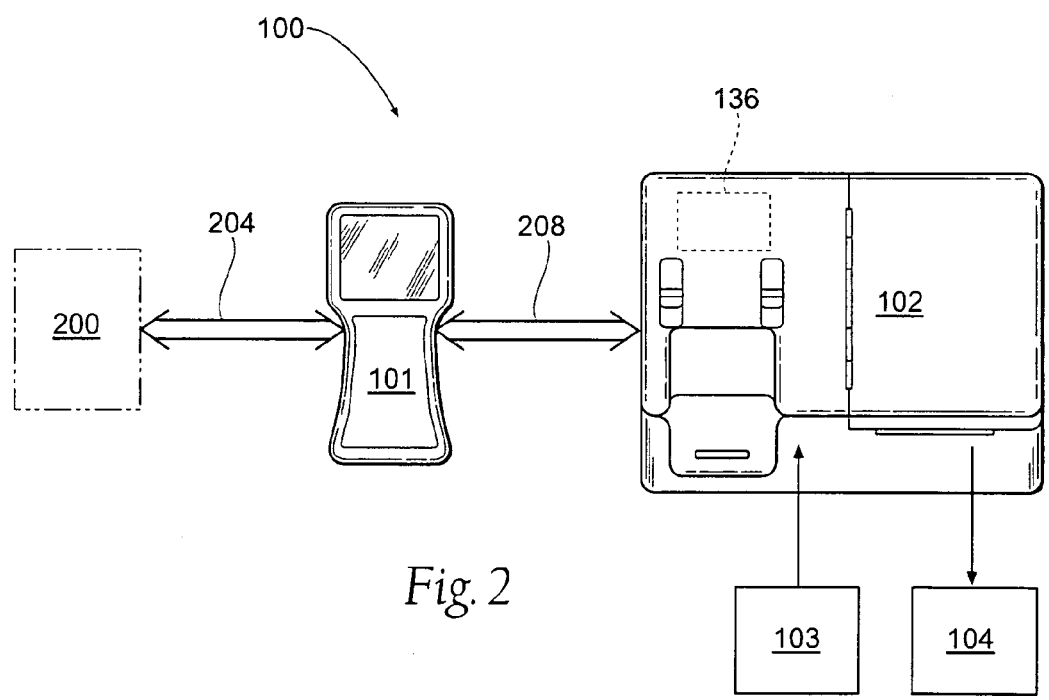
FIG. 2 is a diagrammatic representation of an embodiment of a system according to the present invention.

Referring now to FIG. 2, the embodiment of FIG. 1 is shown diagrammatically. As can further be seen from this figure, the base station 102 may be coupled to the handheld device 101 over a second communication channel 208, thereby allowing performance of various administrative functions, such as battery charging, data back-up, and printing. The base station 102 may have a user input device 103 and a data output device 104. The input device 103 may be, without limitation by way of example, a keyboard, a computer mouse, a digital tablet, a computer network, or the handheld device 101, itself. A plurality of input devices may be used. The data output device 104 may be, without limitation by way of example, a cathode ray tube, a liquid crystal display, a printer, a magnetic disk drive, an optical disk drive, a computer network, or the handheld device 101, itself. A plurality of output devices may be used.

Handheld Device

Figure 3:
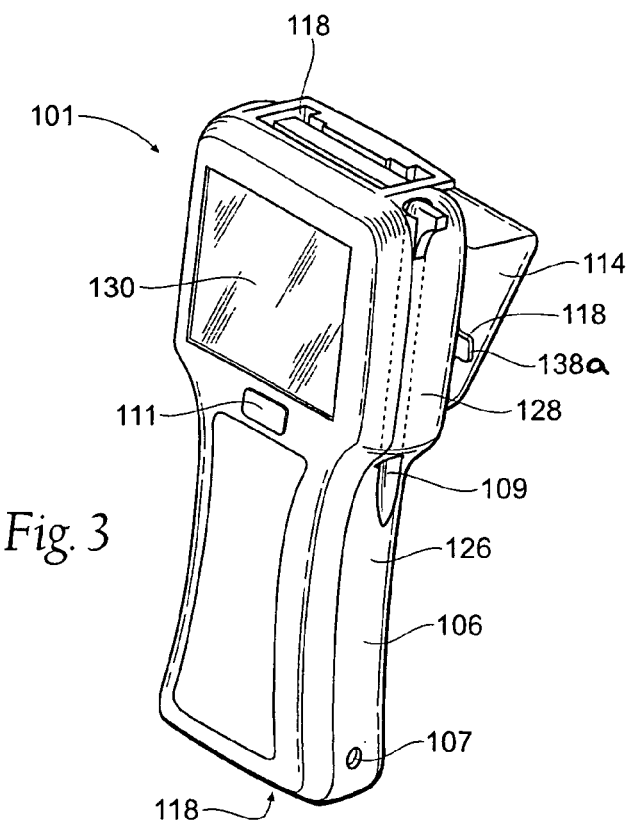
FIG. 3 is a perspective view of a first embodiment of a handheld device according to the system in FIG. 2.
Figure 4:
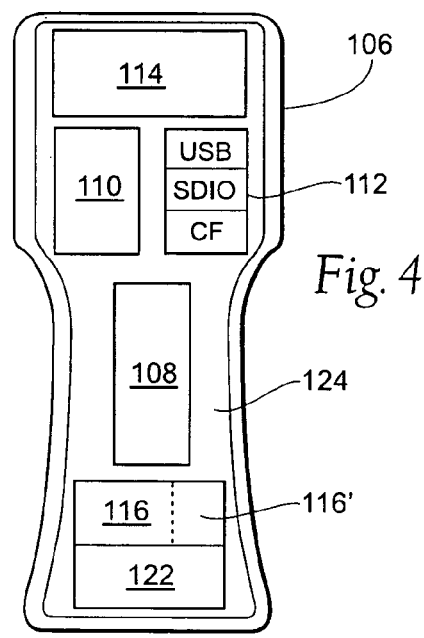
FIG. 4 is a diagrammatic representation of electrical components used in the handheld device of FIG. 3.

Referring to FIGS. 2-4, an embodiment of a handheld device 101 according to the present invention is shown. The handheld device 101 is intended to function as a user interface to a medical device 200, such as an IPG, thereby providing sophisticated operation control and intimate access to the programming of the IPG 200 and patient and system data contained therein. Generally, the handheld device 101 comprises a housing 106 that contains a controller 108, associated memory 110 and communications components 112, a telemetry module 114, a power supply 116, external connection hardware 118, and a user interface 130. Optionally, rather than residing in the housing 106, the telemetry module 114 may be a separate component coupled to the device 101. In addition, the handheld device 101 may further comprise recharging circuitry 122, to enable replenishment of the power supply 116. All of the components may be mounted to 1 or more printed circuit boards 124.

In a representative embodiment, the housing 106 is formed from an impact resistant molded plastic and is adapted to fit comfortably into a user's hand. A desirable size for such adaptation may be 25 centimeters long by 8 centimeters wide by 5 centimeters thick; however, the dimensions may change depending upon how the handheld device 101 is used. The housing 106 may include sections having different widths. That is, the housing 106 may have a first section 126 comprising a narrower width for comfortable placement in a user's hand contrasted to a second section 128 comprising a wider width for accommodation of certain features, such as a screen 130 of desirable size. The housing 106 generally houses one or more printed circuit boards 124 carrying electrical components such as a microcontroller 108, nonvolatile memory 110, communications transceivers 112, and associated biasing circuitry. External connections 118 are provided through, or extending from, the housing 106 wherever desired to allow physical connection to other electronic devices. The external connection hardware 118 may include a removable media interface such as Compact Flash memory, a communications interface such as a Universal Serial Bus (USB)

interface or conventional serial interface, like an RS-232 interface, or even device support tabs 138a used in docking the handheld device 101 to the base station 102. Additionally, user interface mechanisms may be accessible through the housing 106. For instance, a reset button 107 may be available by use of a special tool, such as a stylus 109. Also, it is contemplated that a power button 111 provides user access through the housing 106 to command system power.

The microcontroller 108 in the handheld device 101 is responsible for running system software, as well as application software. While these tasks may be divided amongst multiple controllers, a single controller 118 is desirable. Representative system software is Microsoft Corporation's Windows CE®. Additional system software features, such as peripheral interfaces, are optional and dependent on the software approach used. Associated with the microcontroller 108 is some sort of electronic memory 110. A desirable memory 110 includes nonvolatile random access memory. Nonvolatile memory provides insurance against loss of data in a situation where power is lost and facilitates an extremely low power or zero power inactive (sleep) state of the microcontroller 108. The nonvolatile memory element 110 is capable of storing patient records, arranged by visit or other desirable characteristics, so that a clinician using the handheld device 101 can quickly establish a historical perspective on patient treatment. The nonvolatile memory element 110 may also store all or part of operating system software, application software, or data for the general use of the microcontroller 108.

The device 101 also has a communications module 114 for communicating with the IPG 200 or other medical device. The communications module 114 may be a telemetry module, which is a protocol translator and radio frequency modem that accepts packets from the microcontroller 108 and converts it into wireless messages directed to the IPG 200. The telemetry module 114 is capable of communicating with individual medical devices 200 within its immediate range and desirably up to six feet away. The telemetry module 114 may implement a variety of communication protocols, such as those standard in the art, or custom communication protocols, which may be predetermined by the capabilities of the medical device 200 to which communications must be sent. The communications module 114 may be disabled while the handheld device 101 is docked on the base station 102.

The device 101 further includes a power supply 116, which provides the required electrical power for desired electronic circuit operation. In one embodiment, a primary power supply 116 may be a rechargeable lithium ion battery. Lithium ion batteries are capable of providing many hours of operation without having to be docked to recharge. For instance, it may be desirable to provide a power supply 116 capable of providing eight hours of use without the need for recharge. While the specific functionality of the device 101 during runtime will affect battery requirements, an acceptable power supply 116 may be a rechargeable lithium ion battery having a capacity of 2600 milliamp hours. The device 101 may also have a backup battery 116' capable of maintaining program or data memory in the event of a deep discharge or replacement of the primary battery 116. If a rechargeable power supply 116 is used, proper recharging circuitry 122 may be included in the system 100. Such circuitry 122 may be contained within the handheld device 101, as shown, or may reside in the base station 102.

External connection hardware 118 is also provided on the handheld device 101, thereby providing additional input/output capability. Providing data input/output capability, the device may have at least one universal serial bus (USB) port and/or serial communications port, and other ports as needed to communicate with an externally located telemetry module 114 and the base station 102. Also, external connections 118 may be provided to allow the controller 108 of the handheld device 101 to control the base station 102 operation, for example printer operations, in addition to controlling the handheld device 101.

The device 101 further provides a user interface to the IPG 200, so that a clinician can change control parameters in and view data from the IPG 200. In this manner, a clinician may configure parameters in the individual IPG 200 that adjust application limits for a patient user interface to the IPG 200. A patient user interface provides a limited range of programmability for a medical device. For example, a simple patient user interface may be a device having a single button to turn an IMD on or off. In one embodiment, the clinician user interface is a pressure sensitive touch screen 130 incorporated into the handheld device 101. The device 101 may be controlled by use of the stylus 109 on the screen 130. The screen 130 may be a color display screen supporting a fixed or variable pixel resolution. A desirable pixel resolution may be at least 240×240. The embedded operating system software and screen 130 may support both vertical and horizontal viewing.

The handheld device 101 further may implement a system of checks, balances, and redundancies to qualify and prevent the use of unsafe combinations of settings.

Figure 5:
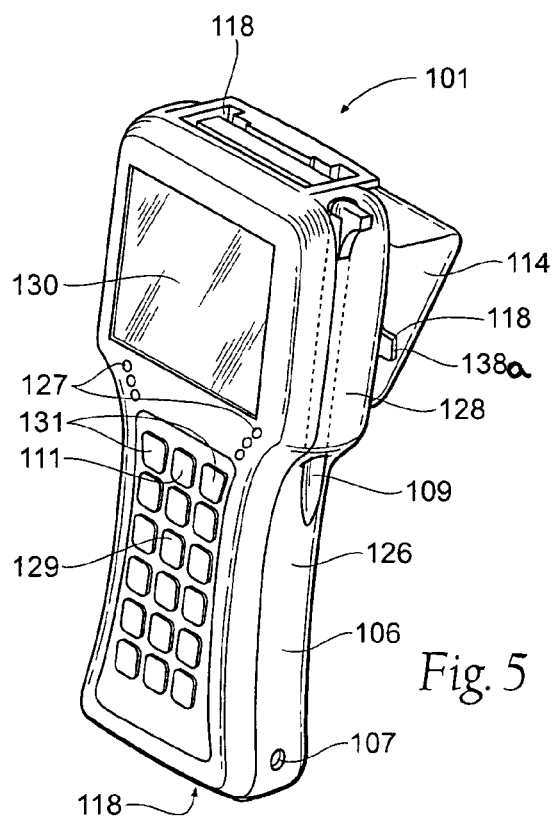
FIG. 5 is a perspective view of a second embodiment of a handheld device according to the system in FIG. 2.

FIG. 5 shows a second embodiment of handheld device 101 according to the present invention where, in addition to or instead of the touch screen 130, the housing 106 may be provided with an on-board keypad 129 and programmable function keys 131 as means of data entry and device control. Programmable function keys 131, as generally understood in the art, may be physical buttons or specific pixel array on the display 130, the functionality of which is not dedicated but rather may change, depending upon the state of the software. Further, the device 101 may include one or more indicators 127, which signal predetermined conditions to a user.

Generally, two approaches may be desirable for implementation of the handheld device 101. The first approach entails modification and adaptation of an off-the-shelf personal digital assistant (PDA) or other portable computer. If adopted, the first approach may require further encasing the PDA in the housing 106 along with a communications module 114 or providing connectivity for such communications module 114 to the PDA. The second approach may encapsulate a customized printed circuit board 124 and component combination in a customized housing 106. This second approach provides more design flexibility than the first approach and allows tighter control over system components. Whichever approach is desirable, the handheld device 101 may function as a single purpose device. That is, the handheld device 101 may serve only in the system 100, rather than provide general purpose computing functionality.

Base Station

Figure 6:
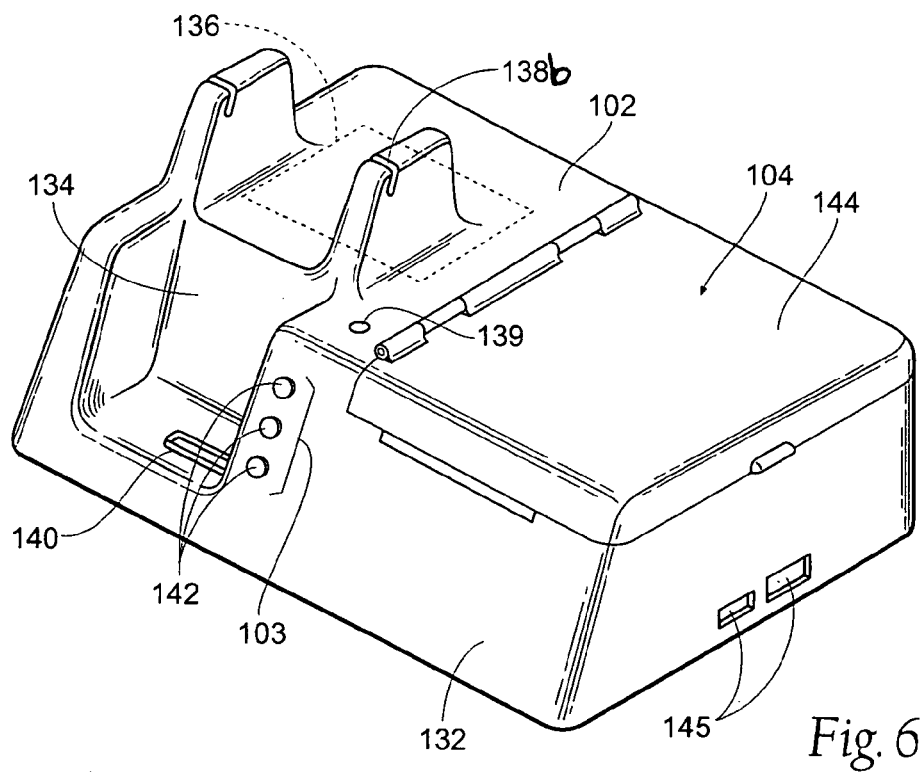
FIG. 6 is a perspective view of a first embodiment of a base station according to the system in FIG. 2.
Figure 7:
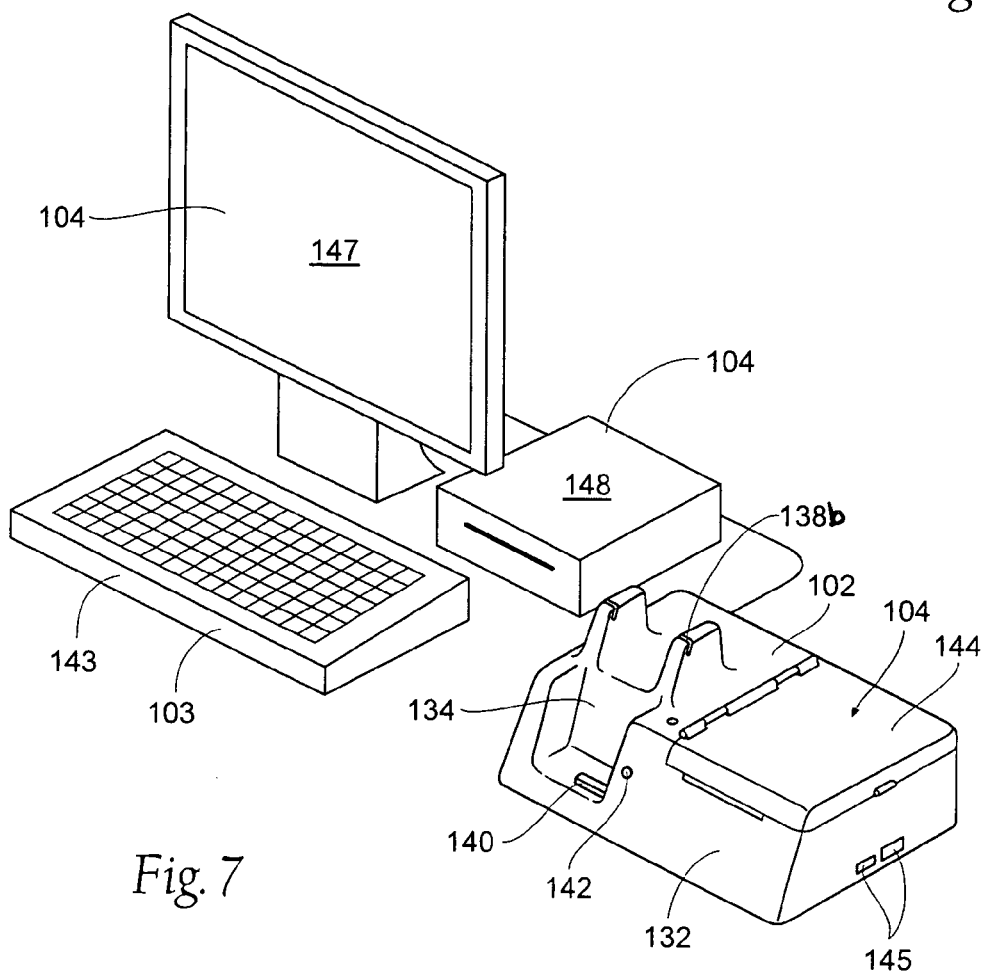
FIG. 7 is a perspective view of a second embodiment of a base station according to the system in FIG. 2.

Referring now to FIGS. 2, 6 and 7, an embodiment of a base station 102 according to the present invention is shown. The base station 102 comprises a base station housing 132, a cradle 134 for holding the handheld device 101, and electronic memory 136. Furthermore, the base station 102 may comprise connectivity for other user input devices 103 and a data output device 104. Alternatively, the base station 102 may contain a user input device 103 and a user output device 104. Each component is described in greater detail below.

The base station housing 132 is of any desirable shape. Adaptation may provide stability on a relatively horizontal surface, such as a desk, or on a relatively vertical surface, such as a wall. The housing 132 generally provides a protective cover for desirable electrical components. Desirable components may be those required to carry out functions such as data backup and restore for the handheld device 101, printing of reports or records for affixing hard copies of information to a patient's chart, power recharging of the handheld device 101, entry of patient data, and export and import of data.

The cradle 134 provides a docking point for the handheld device 101. While connectivity to the handheld device 101 could be provided generally anywhere proximate the base station 102, connectors 140 for power and communication to the handheld device 101 may be provided in the cradle 134.

A user input device 103 may be present in the form of a user interface 142, which allows user intervention and control of the base station 102 functionality. While depicted as discrete buttons 142 on the base station 102, user input may also be achieved through the use of any combination of a standard QWERTY computer keyboard, a computer mouse, or even a custom keyboard. If the microcontroller in the handheld device 101 provides, in addition to control of the handheld device 101, system control for the base station 102, a keyboard 143 may serve as the user input device 103 through the base station 102 to the handheld device 101 through the cradle 134. Furthermore, rather than provide a distinct user input device 103 on or connected to the base station 102, the handheld device 101, itself, may serve as the user input device 103. When the handheld device 101 is docked in the base station 102, the visual display 130 on the handheld device 101 may serve as the user input device 103 to access the base station 102 and any output device 104 connected thereto. As depicted in FIG. 5, the handheld device 101 may also have an on-board keyboard 129 that can be used for data entry. User input to the base station 102 may also be entered through the handheld device screen 130 by way of a stylus 109. It may be desirable to provide storage 139 of the stylus somewhere on the base station 102 or on the handheld device 101 so that it is easily accessible to the user. Positioning of the cradle 134 in the base station 102 may be determined on a basis of ergonomic considerations such as reach and viewing angle.

The base station 102 also includes, or provides connectivity for, a data output device 104. The data output device 104 may comprise a printer 144 to provide hard copy documentation on paper 146 or other substrate suitable for placing into a patient's medical chart. A suitable printer 144 may be a four inch label printer, such as an OEM kiosk printer, that may be mounted on or in the base station 102. Rather than have the printer 144 mounted to the base station 102, a data output device 104 may be connectable to the base station 102. Connectivity of the base station 102 to external devices may be achieved in any desirable way, such as through the use of ports 145. Ports 145 that may be desirable are USB connections or a digital video connection if the output device 104 is a computer monitor 147. A computer monitor 147 may provide an enhanced visual display for the user. The specific technology of the output device 104 is not important; however, if a printer 144 is used, it may employ a thermal print element, inkjet or even impact/ribbon technology.

Data backup may be achieved through the use of computer readable electronic memory 136. The memory 136 may be of any desirable type, including by way of example nonvolatile random access memory, magnetic data storage, optical data storage, or media such as so called flash drives, or other memory types not yet invented.

Figure 8:
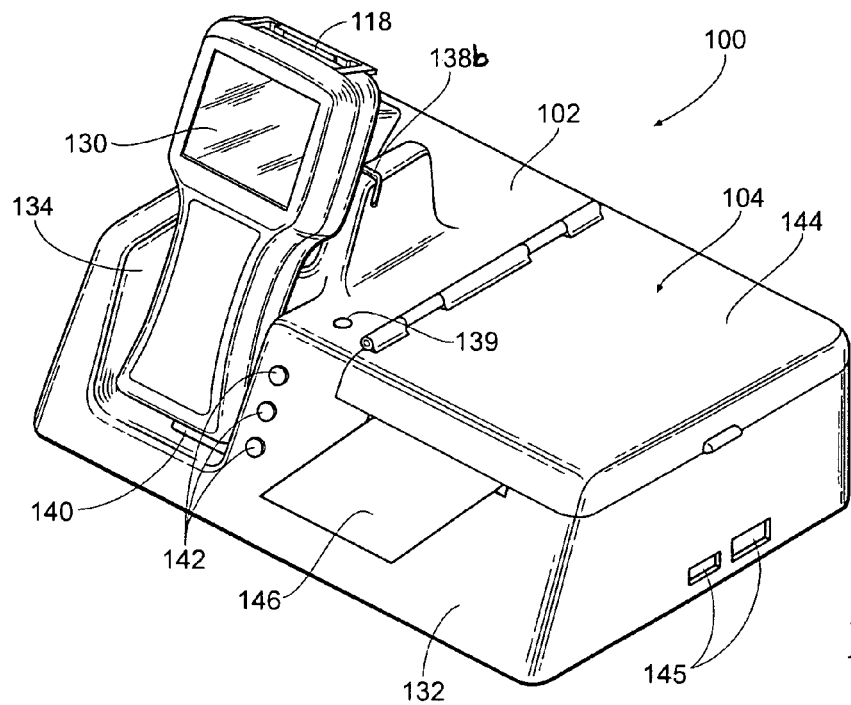
FIG. 8 is a perspective view of the first embodiment of a base station having the handheld device of FIG. 3 docked thereto.
Figure 9:
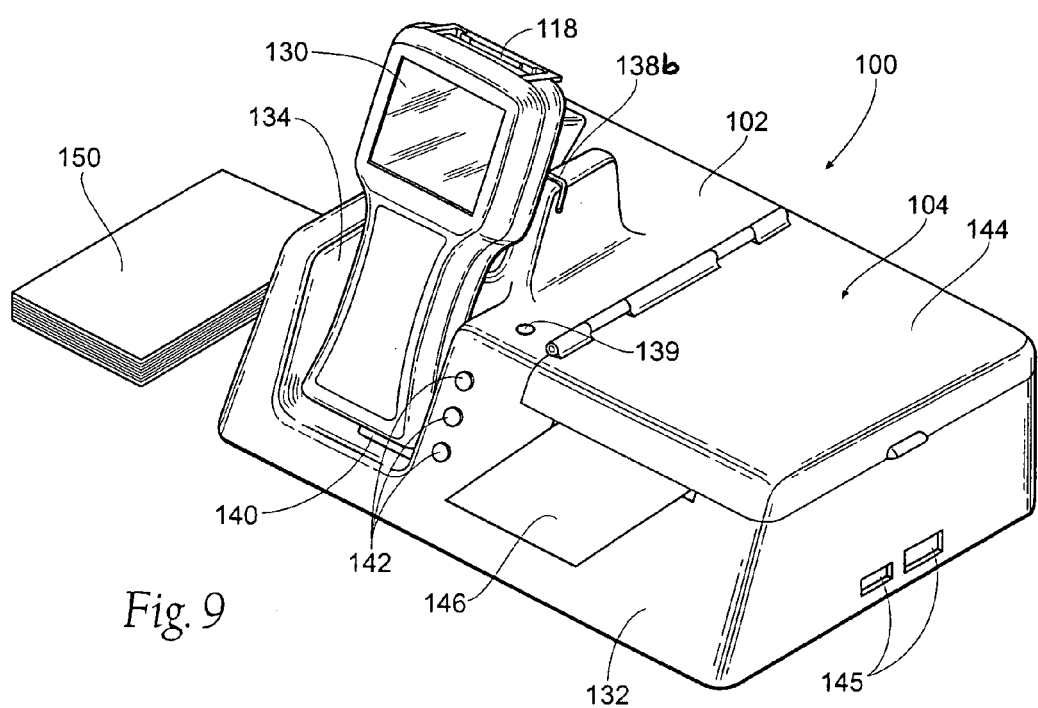
FIG. 9 is a perspective view of the system in FIG. 8 and further including an instruction manual.

FIG. 8 depicts an embodiment of a system 100 according to the present invention comprising a base station 102 shown with a handheld device 101 docked thereto. The position of the cradle 134 is not critical, and the handheld device 101 may rest in the cradle 134 in such a way that the device is positioned conveniently for user viewing, keypad-screen control and data input. A docking support 138b may also be provided, to receive the device support tabs 138a to keep the device 101 in place when docked in the base station 102. If positioning of the screen 130 is a different orientation while in the cradle 134 as opposed to when the device 101 is used outside of the cradle 134, the device support tabs 138a may physically contact the docking support 138b and signal to the handheld device software that the orientation of the image on the display 130 needs to be altered. The LCD screen 130 may function both as a user input device 103 to the base station 102 and as a data output device 104 from the base station 102. The cradle 134 may also have an adjustable viewing angle. As elaborated below, the system 100 may be provided with accompanying documentation 150, as shown in FIG. 9.

Software

Figure 10:
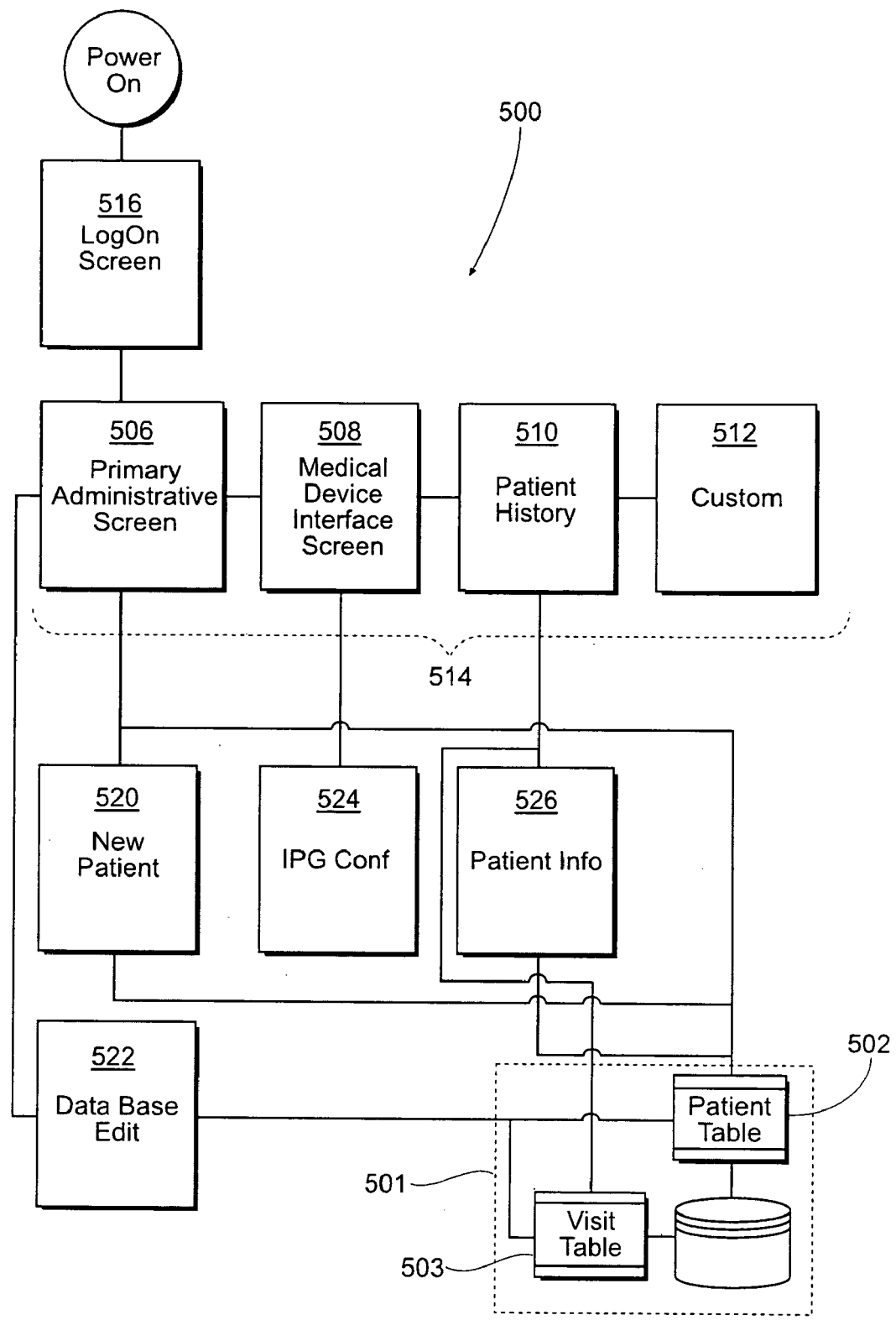
FIG. 10 is a flow chart of an embodiment of the method of software control for programming and logging device data according to an embodiment of the present invention.

In addition to physical systems, the present invention contemplates methods of establishing a communication link with a medical device, retrieving medical device data, programming the medical device, logging medical device data or parameters, and archiving information. Additionally, prior to establishing a communication link with a medical device, the method may include the steps of determining whether any medical devices are within a scannable range and selecting a medical device with which to establish the communications link. Archiving information may include recording data on a variety of media, such as recording on computer readable media or printing on paper. Some or all of the steps can occur automatically by way of software, initiated by an event such as inserting the handheld computer into the base station, or by human intervention in conjunction with the software. An embodiment 500 of a user interactive method is shown in FIG. 10. As shown, the steps are carried out by application software, but are generally initiated by a user of the handheld device 101.

In a representative embodiment, the application software included on the handheld device provides the full range of the clinician experience—from initial patient engagement to documentation and retrieval of patient visits. Although the software may exist in any programming language adaptable to the specific microcontroller, C# (C sharp) is preferred due to its tendency towards rapid development, its C-like syntax, its object orientation, and the high degree of reliability of developed applications. The application software may run on top of the system software that is loaded into the handheld device 101.

The application software interfaces with a database 501. The database 501, which encodes patient names, visits, and other data, may be implemented using Microsoft® structured query language (SQL) Mobile Edition having desirable data backup and restore features. Regardless of the type of database 501, a database interface may be installed on the handheld device 101 as part of the application software install. The database interface allows a user to access patient data from the database 501. Access to patient data may be achieved by entering patient-identifying information. Such data may consist only of patient contact information or may include complex historical patient data and time stamped medical device data. The database 501 containing comprehensive patient information may reside on the handheld device 101 directly. Alternatively, the database 501 may reside on the base station 102 or a hospital computer network. If the database 501 does not reside on the handheld device 101, a temporary data construct containing data fields similar to those in the database 501 is preferred, which allows storage of data for several, but not necessarily all, patients on the handheld device 101.

The database 501 may include several tables. One embodiment may implement two tables: a Patient Table 502, and Visit Table 503. The Patient Table 502 contains all patient information that is relatively constant. The purpose of the Visit Table 503 is to record and store relevant IPG data that would be collected over a series of visits. The user may then display trend or comparative data in graphical formats. Fields of data in the respective tables 502,503 may be hard coded, or reconfiguration of the tables 502,503 may be allowed.

Figure 11:
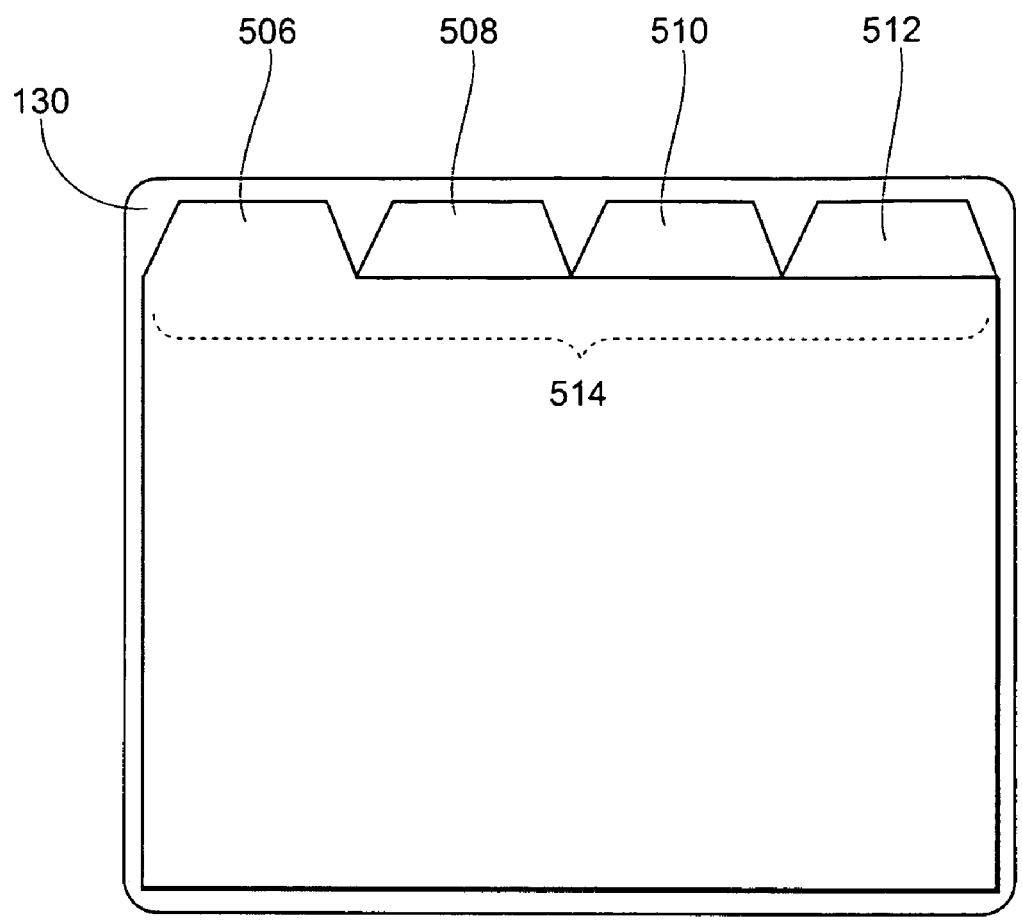
FIG. 11 is an elevation view of a display screen showing the implementation of an embodiment of the method of FIG. 10.

FIG. 10 also shows a navigational relationship of a plurality of displayed application software screens. The number of application screens is not determinative of the present invention. In one embodiment, four main application screens 504 are used: a primary programming and administrative screen 506, an advanced programming screen 508, a patient history screen 510, and a tools screen 512. Users may also add customizable screens as needed for other applications A plurality of screen selectors is displayed on the screen 130 to enable a user to switch the image on the display screen 130 to a different application software screen. That is, on the display screen 130 of the handheld device 101, where an application screen is displayed, a plurality of screen selectors may be provided on the border of the functional screen. As shown in FIGS. 10 and 11, a representative embodiment of the screen selectors is a series of selectable tabs 514. Generally, tabbed screen navigation is well-known in the art. When the desired screen selector 514 is chosen, the appropriate application screen is displayed on the handheld device screen 130. The tab control 407 methodology allows for faster screen loading and more visible navigational choices. User interface functionality on the various screens may be predetermined and remain relatively static, or the functions included on the particular screens may change depending upon frequency of use or other desired operating characteristics. For ease of description, a relatively static implementation is described.

Referring again to FIG. 10, when the handheld device is powered on, a logon screen 516 is displayed. The software may be under revision control and the revision level may be displayed on the logon screen 516. To proceed past the logon screen 516, a user may be prompted to verify that he or she has authority to do so. Due to the sensitive nature of medical information, to enhance patient privacy, and perhaps to comply with appropriate privacy guidelines, the system may control access to its data and functions through a protection scheme. The protection scheme may be a relatively simple text password implemented in software, or a more complicated scheme of data protection involving such things as biometric measurements may be employed. Upon authentication, the user is taken to the primary application screen 506.

The primary screen 506 is displayed to a user after user authentication has occurred. The primary screen 506 may group a predetermined number of the most commonly used functions in the system onto a single screen 506. The primary screen 506 provides access to existing patient selection 518, new patient data entry 520 and editing of database records 522. Access to various administrative functions may also be provided via the primary screen 506. To switch between main application screens 504, the tab control 514 is used.

The advanced programming screen 508 provides a user interface to the data and parameters 524 contained in the medical device 200. Examples of medical device data 524 may be an indication of remaining battery charge in the medical device 200, recharge time, and stimulation time. While programmable parameters 524 for various medical devices 200 will differ, representative parameters 524 for an IPG are pulse amplitude, pulse duration and pulse frequency and sequence timing. Additionally, the device interface screen 508 may allow the selection or alteration of limits for any user (patient) adjustable parameters. Furthermore, a set of predetermined parameters or collections of parameters based on common electrophysiological behavior may be preloaded to minimize the effort on the part of the user. Also, after recognizing programmed parameters, the handheld device 101 may recommend parameters to the user.

The patient history screen 510, allows access to existing patient data 526 drawn from the database 501 and entry of new patient visit information, including textual diary data. Once the patient data 526 has been configured, the patient may automatically be identified during his or her next session and relevant historical data may be made available during subsequent patient visits. Rather than automatic identification, the device 101 may be programmed with the proper communications information or a clinician may query a range of medical device identifiers. During a session with a patient, the software may notify the clinician if communications 204 is interrupted or another medical device 200 intrudes on the session. To avoid the potential for incorrectly or incompletely communicating with medical devices, the communications protocol between the handheld device and any medical device may include the identification of which medical device is being addressed by way of, for example, a unique electronic signature or device serial number.

A tools screen 512 is provided to enable modification of system parameters such as accessibility passwords and date and time functions. Also, the tools screen 512 may provide access to the database 501 as well as base station 102 functionality such as printing. Further, the tools screen 512 may provide medical device query capability, thus allowing the device 101 to scan a predetermined area for responsive medical devices 200.

A customizable screen, or plurality of customizable screens, may also be desired, the functionality of which can be tailored to a specific user's operating procedures or tailored applications. Alternatively, the customizable screen may be a screen that is available only when the handheld device 101 is docked in a base station 102.

Some functionality may be desirable no matter which screen is displayed. That is, the application software may monitor the occurrence of hardware faults and also monitor battery level. When predetermined events occur, the handheld device 101 may emit a warning, such as a visual or audio warning, when a hardware fault occurs or if the battery charge for either the telemetry module 114 or handheld device 101 is at a predetermined level. Also, an extensive help menu system may be incorporated. The help menu may be accessible from any displayed screen, perhaps as a separate tab control 514.

Although the handheld device 101 application software provides the ability to download patient data from a database 501, a clinician may have the option of using the handheld device 101 without having patient data available. That is, if all patient data is erased off the handheld device 101 or otherwise not entered, the device 101 may still function as a user interface to the medical device 200. This may require the user to enter at least a default set of patient data, such as patient last name or medical device code.

System Use

The system 100 may be constructed for safe operation within an operating room and desirably does not interfere with any hospital electronic equipment. While it is generally expected that only the handheld device 101 will be used in the operating room, a base station 102 may also be located in an operating room. When the handheld device 101 is used in an operating room or other location where sterility is of utmost importance, the device 101 can be sterilized, or a sterile device cover may be provided to enclose or shield the device 101.

A clinician can use the handheld device 101 in an operating room to turn on an IPG 200 and adjust stimulus parameters in the IPG 200. The clinician simply enters predetermined patient data to be associated with the IPG 200 that is in the process of being programmed. The clinician who is using the handheld device 101 may be the surgeon who has placed the IPG 200, a physician's assistant, a nurse, or other clinician authorized to do so. It is to be appreciated that the handheld device 101, through a wireless range, may be used outside of the sterile field.

In addition to use in an operating room, a clinician may use the system 100 in an office setting when a patient returns for follow-up visits. The handheld device 101 allows a clinician to interrogate the IPG 200 for compliance data such as recharge history and current stimulus parameter settings. The clinician may make adjustments to the stimulus parameters as necessary based on the feedback from the patient. The clinician may also schedule upcoming appointments in the handheld device 101 and recall any details of past appointments.

To ensure reliable and robust operation, the system, at least while certain software is active, may be a single purpose device. Although not a required feature, the system may have the ability to connect to a hospital computer network or directly interface to other devices such as an external disk drive 148, as shown in FIG. 7. The disk drive 148 may comprise a hard magnetic disk drive or a drive capable of reading or writing removable media, such as magnetic or optical disks or non-volatile semiconductor memory cards or sticks. As shown in FIG. 9, the system 100 may be provided with all appropriate documentation 150 that conforms to relevant guidelines and further conforms to health and safety requirements as defined by the appropriate regulatory bodies. In addition to complying with guidelines mandated by regulatory bodies, the documentation 150 may include printed or computer readable instructions 150, which provide guidance on such things as the use of the system, data recovery techniques, and elaborate on the features provided. The features may be general to a system according to the present invention or predetermined custom features may be described in detail.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A system comprising:
   a handheld electronic device, the device configured to communicate with an implantable medical device; and
   a base station,
   wherein the handheld electronic device is further configured to communicate with the base station, and
   wherein the handheld electronic device includes a user interface that is configured to serve as a user input device of the base station, such that when the handheld electronic device is docked to the base station the user interface of the handheld electronic device serves as the user input device of the base station in order to access the base station and any output device that is connected to the base station,
   wherein the user interface of the handheld electronic device controls both the handheld electronic device and also the base station, and wherein the user interface of the handheld electronic device comprises a display screen that further functions as a data output device from the base station.

2. A system according to claim 1, wherein the medical device is adapted to deliver a therapy.

3. A system according to claim 2, wherein the medical device comprises an implantable pulse generator.

4. A system according to claim 1, wherein the base station comprises a housing and a handheld device connector, wherein the handheld device connector is configured to dock the handheld electronic device to the base station.

5. A system according to claim 4, wherein the base station housing is adapted to sit on a substantially horizontal support surface.

6. A system according to claim 4, wherein the base station housing is adapted to be supported on a substantially vertical support surface.

7. A system according to claim 4, wherein the base station further comprises a data output device.

8. A system according to claim 1, wherein the base station includes a computer-readable memory storing a database that contains patient data and medical device data.

9. A system according to claim 1, wherein an input through the user interface of the handheld electronic device operates the base station resulting in an output to the user interface of the handheld electronic device from the base station.

10. A system for programming an implantable medical device and archiving data or parameters of the implantable medical device, the system comprising:
    a handheld unit, the handheld unit comprising:
       a handheld unit housing;
       a power supply seated in the handheld unit housing;
       a user interface disposed at least partially in the handheld unit housing;
       a microprocessor electronically coupled to the power supply and the user interface;
       a telemetry module electronically coupled to the power supply and the microprocessor, wherein the telemetry module provides a communications link with the implantable medical device; and
       external connection hardware;
    a base station, the base station comprising:
       a base station housing having a handheld device cradle; and
       electronic memory,
    wherein the handheld device cradle in the base station housing is configured to receive at least a portion of the external connection hardware of the handheld unit, and
    wherein the user interface of the handheld unit is further configured to serve as a user input device of the base station, such that when the handheld unit is docked within the handheld device cradle of the base station housing, the user interface of the handheld unit serves as the user input device of the base station in order to access the base station and any output device that is connected to the base station,
    wherein the user interface of the handheld unit controls both the handheld unit and also the base station, and wherein the user interface of the handheld unit comprises a display screen that further functions as a data output device from the base station.

11. A system according to claim 10, wherein the user interface is also electronically coupled to the power supply.

12. A system according to claim 10, wherein the base station further includes a computer-readable memory storing a database that contains patient data and medical device data.

13. A system according to claim 10, wherein an input through the user interface of the handheld unit operates the base station resulting in an output to the user interface of the handheld unit from the base station.

* * * * *